(12) United States Patent
Rossetto et al.

(10) Patent No.: US 12,167,893 B2
(45) Date of Patent: *Dec. 17, 2024

(54) SYSTEMS AND METHODS FACILITATING PRE-OPERATIVE PREDICTION OF POST-OPERATIVE TISSUE FUNCTION

(71) Applicant: Covidien LP, Mansfield, MA (US)

(72) Inventors: Francesca Rossetto, Longmont, CO (US); Joe D. Sartor, Longmont, CO (US)

(73) Assignee: Covidien LP, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/229,352

(22) Filed: Aug. 2, 2023

(65) Prior Publication Data
US 2023/0404674 A1   Dec. 21, 2023

Related U.S. Application Data

(63) Continuation of application No. 16/719,172, filed on Dec. 18, 2019, now Pat. No. 11,744,643.

(60) Provisional application No. 62/801,191, filed on Feb. 5, 2019, provisional application No. 62/800,670, filed on Feb. 4, 2019.

(51) Int. Cl.
*A61B 34/10* (2016.01)
*G06T 7/00* (2017.01)
*G06T 19/00* (2011.01)

(52) U.S. Cl.
CPC .......... *A61B 34/10* (2016.02); *G06T 7/0012* (2013.01); *A61B 2034/105* (2016.02); *A61B 2034/107* (2016.02); *G06T 19/003* (2013.01); *G06T 2207/30061* (2013.01)

(58) Field of Classification Search
CPC ............... A61B 34/10; A61B 2034/10; A61B 2034/105

See application file for complete search history.

(56) References Cited

U.S. PATENT DOCUMENTS

| | | | |
|---|---|---|---|
| 5,057,494 A | 10/1991 | Sheffield | |
| 5,321,113 A | 6/1994 | Cooper et al. | |
| 6,003,517 A | 12/1999 | Sheffield et al. | |
| 6,327,490 B1 | 12/2001 | Spetz | |
| 6,360,116 B1 | 3/2002 | Jackson, Jr. et al. | |
| 6,539,247 B2 | 3/2003 | Spetz | |
| 7,574,251 B2 | 8/2009 | Lu et al. | |

(Continued)

FOREIGN PATENT DOCUMENTS

| | | | |
|---|---|---|---|
| BR | 0013237 A | 7/2003 | |
| BR | 0116004 A | 6/2004 | |

(Continued)

OTHER PUBLICATIONS

Extended European Search Report issued in European Patent Application No. 20155199.1 dated Jul. 3, 2020, 7 pages.

*Primary Examiner* — Ryan McCulley
(74) *Attorney, Agent, or Firm* — Weber Rosselli & Cannon LLP

(57) ABSTRACT

Systems and methods that facilitate the pre-operative prediction of post-operative tissue function to assist a clinician in planning for and carrying out a surgical procedure. In particular, systems and methods that facilitate the pre-operative prediction of post-resection lung tissue function, thus assisting a clinician in determining the location(s) and volume(s) of lung tissue to be resected.

20 Claims, 6 Drawing Sheets

(56) References Cited

U.S. PATENT DOCUMENTS

| | | |
|---|---|---|
| 7,616,735 B2 | 11/2009 | Maciunas et al. |
| 7,639,854 B2 | 12/2009 | Schnarr et al. |
| 7,773,788 B2 | 8/2010 | Lu et al. |
| 7,801,271 B2 | 9/2010 | Gertner et al. |
| 7,815,561 B2 | 10/2010 | Forman et al. |
| 7,831,289 B2 | 11/2010 | Riker et al. |
| 7,831,293 B2 | 11/2010 | Ellis et al. |
| 7,899,517 B2 | 3/2011 | Kindlein et al. |
| 8,070,752 B2 | 12/2011 | Metzger et al. |
| 8,150,497 B2 | 4/2012 | Gielen et al. |
| 8,241,293 B2 | 8/2012 | Stone et al. |
| 8,265,949 B2 | 9/2012 | Haddad |
| 8,301,228 B2 | 10/2012 | Kindlein et al. |
| 8,335,359 B2 | 12/2012 | Fidrich et al. |
| 8,414,123 B2 | 4/2013 | Boukhny et al. |
| 8,428,315 B2 | 4/2013 | Suetens et al. |
| 8,473,305 B2 | 6/2013 | Belcher et al. |
| 8,484,001 B2 | 7/2013 | Glozman et al. |
| 8,532,807 B2 | 9/2013 | Metzger |
| 8,538,543 B2 | 9/2013 | McIntyre et al. |
| 8,706,184 B2 | 4/2014 | Mohr et al. |
| 8,744,553 B2 | 6/2014 | Kindlein et al. |
| 8,792,614 B2 | 7/2014 | Witten et al. |
| 8,821,499 B2 | 9/2014 | Iannotti et al. |
| 8,827,934 B2 | 9/2014 | Chopra et al. |
| 8,828,087 B2 | 9/2014 | Stone et al. |
| 8,880,145 B2 | 11/2014 | Cacique et al. |
| 8,903,530 B2 | 12/2014 | Metzger |
| 8,942,446 B2 | 1/2015 | Martens |
| 8,979,871 B2 | 3/2015 | Tyc et al. |
| 9,005,297 B2 | 4/2015 | Katrana et al. |
| 9,011,452 B2 | 4/2015 | Iannotti et al. |
| 9,089,382 B2 | 7/2015 | Hochman et al. |
| 9,099,015 B2 | 8/2015 | Liang et al. |
| 9,113,971 B2 | 8/2015 | Metzger et al. |
| 9,129,054 B2 | 9/2015 | Nawana et al. |
| 9,198,733 B2 | 12/2015 | Neal et al. |
| 9,238,151 B2 | 1/2016 | Riley et al. |
| 9,259,287 B2 | 2/2016 | Mansi et al. |
| 9,277,970 B2 | 3/2016 | Mansi et al. |
| 9,289,144 B2 | 3/2016 | Lujan et al. |
| 9,289,253 B2 | 3/2016 | Vanasse et al. |
| 9,308,254 B2 | 4/2016 | Maze et al. |
| 9,320,421 B2 | 4/2016 | Chabanas et al. |
| 9,345,548 B2 | 5/2016 | Schoenefeld et al. |
| 9,375,268 B2 | 6/2016 | Long |
| 9,381,377 B2 | 7/2016 | Kindlein et al. |
| 9,439,623 B2 | 9/2016 | Frank et al. |
| 9,439,627 B2 | 9/2016 | Case et al. |
| 9,456,765 B2 | 10/2016 | Odermatt et al. |
| 9,474,588 B2 | 10/2016 | Hochman et al. |
| 9,510,909 B2 | 12/2016 | Grant et al. |
| 9,539,013 B2 | 1/2017 | Katrana et al. |
| 9,600,138 B2 | 3/2017 | Thomas et al. |
| 9,610,021 B2 | 4/2017 | Dvorsky et al. |
| 9,615,840 B2 | 4/2017 | Iannotti et al. |
| 9,655,775 B2 | 5/2017 | Boukhny et al. |
| 9,700,292 B2 | 7/2017 | Nawana et al. |
| 9,700,390 B2 | 7/2017 | Porter et al. |
| 9,734,632 B2 | 8/2017 | Thomas et al. |
| 9,750,493 B2 | 9/2017 | Robinson et al. |
| 9,757,238 B2 | 9/2017 | Metzger |
| 9,761,014 B2 | 9/2017 | Oktay et al. |
| 9,833,245 B2 | 12/2017 | Maxson |
| 9,855,106 B2 | 1/2018 | Jaramaz et al. |
| 9,877,697 B2 | 1/2018 | Yang et al. |
| 9,907,659 B2 | 3/2018 | Belcher et al. |
| 9,918,659 B2 | 3/2018 | Chopra et al. |
| 9,918,740 B2 | 3/2018 | Uthgenannt et al. |
| 9,922,417 B2 | 3/2018 | Sela et al. |
| 9,936,887 B2 | 4/2018 | Dvorsky et al. |
| 9,993,305 B2 | 6/2018 | Andersson |
| 9,999,772 B2 | 6/2018 | Venkatesan |
| 10,004,558 B2 | 6/2018 | Long et al. |
| 10,124,114 B2 | 11/2018 | Raghavan et al. |
| 10,166,019 B2 | 1/2019 | Nawana et al. |
| 10,179,032 B2 | 1/2019 | Andersson |
| 10,194,897 B2 | 2/2019 | Cedro et al. |
| 10,206,695 B2 | 2/2019 | Meridew et al. |
| 10,223,825 B2 | 3/2019 | Embrey |
| 10,226,397 B2 | 3/2019 | Becse et al. |
| 10,251,706 B2 | 4/2019 | Jaramaz et al. |
| 10,255,723 B2 | 4/2019 | Thomas et al. |
| 10,292,770 B2 | 5/2019 | Ryan et al. |
| 10,335,162 B2 | 7/2019 | Maxson |
| 10,335,254 B2 | 7/2019 | Hochman et al. |
| 10,342,821 B2 | 7/2019 | Wager et al. |
| 10,368,948 B2 | 8/2019 | Tripathi |
| 10,373,719 B2 | 8/2019 | Soper et al. |
| 10,376,178 B2 | 8/2019 | Chopra |
| 10,390,845 B2 | 8/2019 | Vanasse et al. |
| 10,402,535 B2 | 9/2019 | Audigier et al. |
| 10,405,753 B2 | 9/2019 | Sorger |
| 10,426,551 B2 | 10/2019 | Gupta et al. |
| 10,433,763 B2 | 10/2019 | Piron et al. |
| 10,478,162 B2 | 11/2019 | Barbagli et al. |
| 10,480,926 B2 | 11/2019 | Froggatt et al. |
| 10,524,866 B2 | 1/2020 | Srinivasan et al. |
| 10,537,390 B2 | 1/2020 | Varadarajan et al. |
| 10,555,788 B2 | 2/2020 | Panescu et al. |
| 10,561,360 B2 | 2/2020 | Amiot et al. |
| 10,569,071 B2 | 2/2020 | Harris et al. |
| 10,575,875 B2 | 3/2020 | Pavlovskaia et al. |
| 10,582,846 B2 | 3/2020 | Raymond et al. |
| 10,582,847 B2 | 3/2020 | Raymond et al. |
| 10,583,039 B2 | 3/2020 | Raymond et al. |
| 10,583,310 B1 | 3/2020 | Fram et al. |
| 10,595,844 B2 | 3/2020 | Nawana et al. |
| 10,603,106 B2 | 3/2020 | Weide et al. |
| 10,610,306 B2 | 4/2020 | Chopra |
| 10,635,924 B2 | 4/2020 | Kamen et al. |
| 10,638,953 B2 | 5/2020 | Duindam et al. |
| 10,639,114 B2 | 5/2020 | Schuh et al. |
| 10,660,709 B2 | 5/2020 | Chaoui |
| 10,674,970 B2 | 6/2020 | Averbuch et al. |
| 10,682,070 B2 | 6/2020 | Duindam |
| 10,702,137 B2 | 7/2020 | Deyanov |
| 10,706,543 B2 | 7/2020 | Donhowe et al. |
| 10,709,506 B2 | 7/2020 | Coste-Maniere et al. |
| 10,772,485 B2 | 9/2020 | Schlesinger et al. |
| 10,796,432 B2 | 10/2020 | Mintz et al. |
| 10,823,627 B2 | 11/2020 | Sanborn et al. |
| 10,827,913 B2 | 11/2020 | Ummalaneni et al. |
| 10,835,153 B2 | 11/2020 | Rafii-Tari et al. |
| 10,885,630 B2 | 1/2021 | Li et al. |
| 2002/0147462 A1 | 10/2002 | Mair et al. |
| 2003/0013972 A1 | 1/2003 | Makin |
| 2004/0120981 A1 | 6/2004 | Nathan |
| 2008/0045938 A1 | 2/2008 | Weide et al. |
| 2011/0093243 A1 | 4/2011 | Tawhai et al. |
| 2013/0303945 A1 | 11/2013 | Blumenkranz et al. |
| 2014/0035798 A1 | 2/2014 | Kawada et al. |
| 2014/0226884 A1 | 8/2014 | Porikli et al. |
| 2014/0275952 A1 | 9/2014 | Monroe et al. |
| 2015/0148690 A1 | 5/2015 | Chopra et al. |
| 2015/0238270 A1 | 8/2015 | Raffy et al. |
| 2015/0265368 A1 | 9/2015 | Chopra et al. |
| 2016/0038247 A1 | 2/2016 | Bharadwaj et al. |
| 2016/0143697 A1 | 5/2016 | Chen et al. |
| 2016/0157939 A1 | 6/2016 | Larkin et al. |
| 2016/0183841 A1 | 6/2016 | Duindam et al. |
| 2016/0192860 A1 | 7/2016 | Allenby et al. |
| 2016/0287344 A1 | 10/2016 | Donhowe et al. |
| 2017/0112571 A1 | 4/2017 | Thiel et al. |
| 2017/0112576 A1 | 4/2017 | Coste-Maniere et al. |
| 2017/0209071 A1 | 7/2017 | Zhao et al. |
| 2017/0265952 A1 | 9/2017 | Donhowe et al. |
| 2017/0311844 A1 | 11/2017 | Zhao et al. |
| 2017/0319165 A1 | 11/2017 | Averbuch |
| 2018/0078318 A1 | 3/2018 | Barbagli et al. |
| 2018/0144092 A1 | 5/2018 | Flitsch et al. |
| 2018/0153621 A1 | 6/2018 | Duindam et al. |
| 2018/0161102 A1 | 6/2018 | Wei et al. |
| 2018/0235709 A1 | 8/2018 | Donhowe et al. |

(56) References Cited

U.S. PATENT DOCUMENTS

| | | |
|---|---|---|
| 2018/0240237 A1 | 8/2018 | Donhowe et al. |
| 2018/0256262 A1 | 9/2018 | Duindam et al. |
| 2018/0263706 A1 | 9/2018 | Averbuch |
| 2018/0279852 A1 | 10/2018 | Rafii-Tari et al. |
| 2018/0325419 A1 | 11/2018 | Zhao et al. |
| 2019/0000559 A1 | 1/2019 | Berman et al. |
| 2019/0000560 A1 | 1/2019 | Berman et al. |
| 2019/0008413 A1 | 1/2019 | Duindam et al. |
| 2019/0038365 A1 | 2/2019 | Soper et al. |
| 2019/0065209 A1 | 2/2019 | Mishra et al. |
| 2019/0110839 A1 | 4/2019 | Rafii-Tari et al. |
| 2019/0175062 A1 | 6/2019 | Rafii-Tari et al. |
| 2019/0175799 A1 | 6/2019 | Hsu et al. |
| 2019/0183318 A1 | 6/2019 | Froggatt et al. |
| 2019/0183585 A1 | 6/2019 | Rafii-Tari et al. |
| 2019/0183587 A1 | 6/2019 | Rafii-Tari et al. |
| 2019/0192234 A1 | 6/2019 | Gadda et al. |
| 2019/0209016 A1 | 7/2019 | Herzlinger et al. |
| 2019/0209043 A1 | 7/2019 | Zhao et al. |
| 2019/0216548 A1 | 7/2019 | Ummalaneni |
| 2019/0239723 A1 | 8/2019 | Duindam et al. |
| 2019/0239831 A1 | 8/2019 | Chopra |
| 2019/0250050 A1 | 8/2019 | Sanborn et al. |
| 2019/0254649 A1 | 8/2019 | Walters et al. |
| 2019/0269470 A1 | 9/2019 | Barbagli et al. |
| 2019/0269818 A1 | 9/2019 | Dhanaraj et al. |
| 2019/0269819 A1 | 9/2019 | Dhanaraj et al. |
| 2019/0272634 A1 | 9/2019 | Li et al. |
| 2019/0298160 A1 | 10/2019 | Ummalaneni et al. |
| 2019/0298451 A1 | 10/2019 | Wong et al. |
| 2019/0320878 A1 | 10/2019 | Duindam et al. |
| 2019/0320937 A1 | 10/2019 | Duindam et al. |
| 2019/0336238 A1 | 11/2019 | Yu et al. |
| 2019/0343424 A1 | 11/2019 | Blumenkranz et al. |
| 2019/0350659 A1 | 11/2019 | Wang et al. |
| 2019/0365199 A1 | 12/2019 | Zhao et al. |
| 2019/0365479 A1 | 12/2019 | Rafii-Tari |
| 2019/0365486 A1 | 12/2019 | Srinivasan et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0008655 A1 | 1/2020 | Schlesinger et al. |
| 2020/0030044 A1 | 1/2020 | Wang et al. |
| 2020/0030461 A1 | 1/2020 | Sorger |
| 2020/0038750 A1 | 2/2020 | Kojima |
| 2020/0043207 A1 | 2/2020 | Lo et al. |
| 2020/0046431 A1 | 2/2020 | Soper et al. |
| 2020/0046436 A1 | 2/2020 | Tzeisler et al. |
| 2020/0054399 A1 | 2/2020 | Duindam et al. |
| 2020/0054408 A1 | 2/2020 | Schuh et al. |
| 2020/0060771 A1 | 2/2020 | Lo et al. |
| 2020/0069192 A1 | 3/2020 | Sanborn et al. |
| 2020/0077870 A1 | 3/2020 | Dicarlo et al. |
| 2020/0078023 A1 | 3/2020 | Cedro et al. |
| 2020/0078095 A1 | 3/2020 | Chopra et al. |
| 2020/0078103 A1 | 3/2020 | Duindam et al. |
| 2020/0085514 A1 | 3/2020 | Blumenkranz |
| 2020/0109124 A1 | 4/2020 | Pomper et al. |
| 2020/0129045 A1 | 4/2020 | Prisco |
| 2020/0129239 A1 | 4/2020 | Bianchi et al. |
| 2020/0138514 A1 | 5/2020 | Blumenkranz et al. |
| 2020/0138515 A1 | 5/2020 | Wong |
| 2020/0142013 A1 | 5/2020 | Wong |
| 2020/0155116 A1 | 5/2020 | Donhowe et al. |
| 2020/0155232 A1 | 5/2020 | Wong |
| 2020/0170623 A1 | 6/2020 | Averbuch |
| 2020/0170720 A1 | 6/2020 | Ummalaneni |
| 2020/0179058 A1 | 6/2020 | Barbagli et al. |
| 2020/0188021 A1 | 6/2020 | Wong et al. |
| 2020/0188038 A1 | 6/2020 | Donhowe et al. |
| 2020/0205903 A1 | 7/2020 | Srinivasan et al. |
| 2020/0205904 A1 | 7/2020 | Chopra |
| 2020/0214664 A1 | 7/2020 | Zhao et al. |
| 2020/0229679 A1 | 7/2020 | Zhao et al. |
| 2020/0242767 A1 | 7/2020 | Zhao et al. |
| 2020/0275860 A1 | 9/2020 | Duindam |
| 2020/0297442 A1 | 9/2020 | Adebar et al. |
| 2020/0315554 A1 | 10/2020 | Averbuch et al. |
| 2020/0330795 A1 | 10/2020 | Sawant et al. |
| 2020/0352427 A1 | 11/2020 | Deyanov |
| 2020/0364865 A1 | 11/2020 | Donhowe et al. |
| 2020/0383750 A1 | 12/2020 | Kemp et al. |
| 2021/0000524 A1 | 1/2021 | Barry et al. |
| 2021/0137634 A1 | 5/2021 | Lang |

FOREIGN PATENT DOCUMENTS

| | | |
|---|---|---|
| BR | 0307259 A | 12/2004 |
| BR | 0412298 A2 | 9/2006 |
| BR | 112018003862 A2 | 10/2018 |
| CZ | 1644519 A | 12/2008 |
| CZ | 486540 B1 | 9/2016 |
| CZ | 2709512 B6 | 8/2017 |
| CZ | 2884879 B1 | 1/2020 |
| EP | 1644519 B1 | 12/2008 |
| EP | 2141497 A1 | 1/2010 |
| EP | 3298976 A1 | 3/2018 |
| EP | 3398552 A1 | 11/2018 |
| EP | 3413830 A4 | 9/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| EP | 3749239 A1 | 12/2020 |
| MX | PA03005028 A | 1/2004 |
| MX | PA03000137 A | 9/2004 |
| MX | PA03006874 A | 9/2004 |
| MX | 225663 B | 1/2005 |
| MX | 226292 B | 2/2005 |
| MX | PA03010507 A | 7/2005 |
| MX | PA05011725 A | 5/2006 |
| MX | 06011286 | 3/2007 |
| MX | 246862 B | 6/2007 |
| MX | 2007006441 A | 8/2007 |
| MX | 265247 B | 3/2009 |
| MX | 284569 B | 3/2011 |
| WO | 2015127355 A1 | 8/2015 |

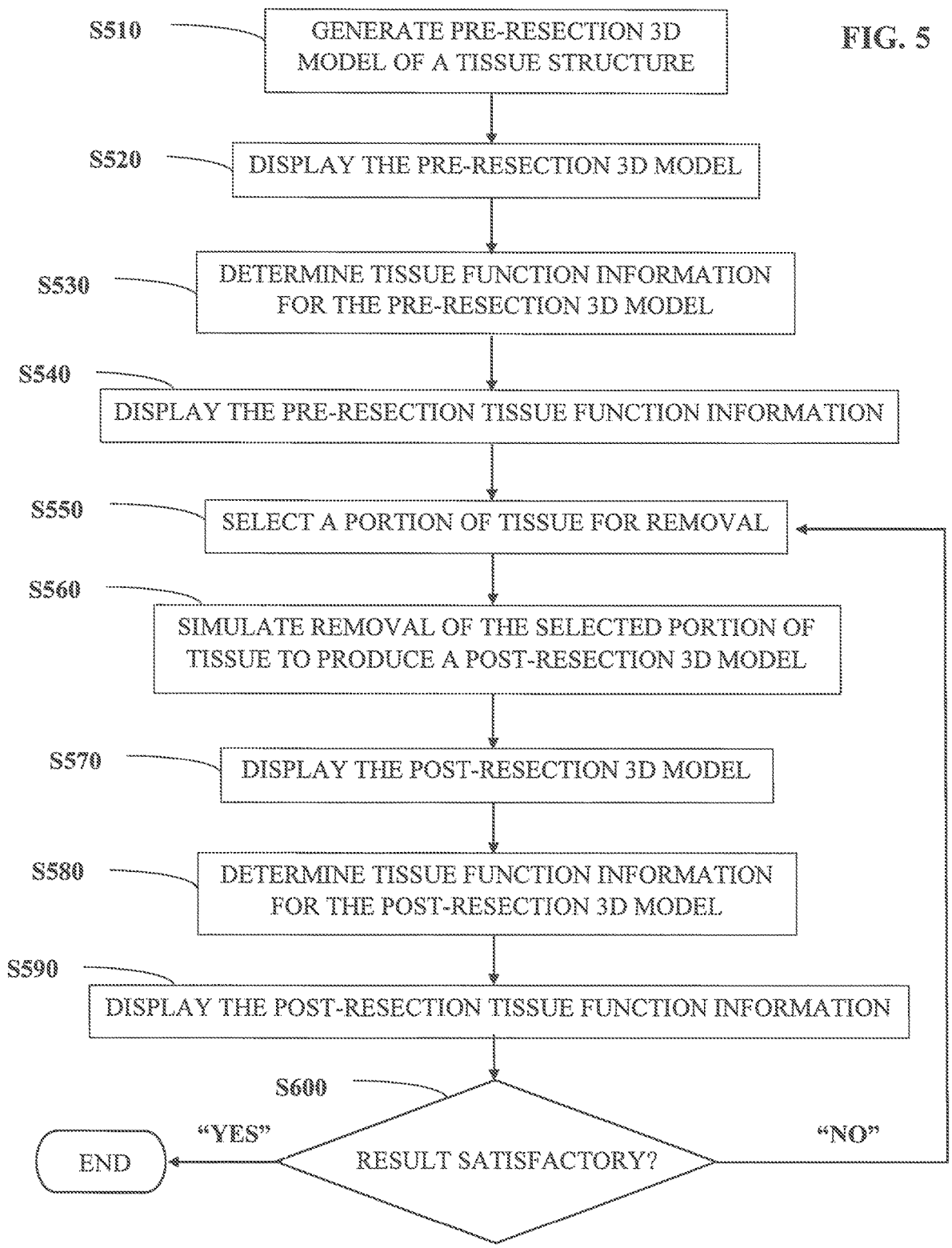

SYSTEMS AND METHODS FACILITATING PRE-OPERATIVE PREDICTION OF POST-OPERATIVE TISSUE FUNCTION

CROSS-REFERENCE TO RELATED APPLICATIONS

This application is a continuation of U.S. patent application Ser. No. 16/719,172, filed on Dec. 18, 2019, which claims the benefit of, and priority to, U.S. Provisional Patent Application Ser. No. 62/801,191, filed on Feb. 5, 2019 and U.S. Provisional Patent Application Ser. No. 62/800,670, filed on Feb. 4, 2019, the entire content of each of which is hereby incorporated by reference herein.

FIELD

The disclosure relates to surgical systems and methods, and more particularly, to systems and methods facilitating pre-operative prediction of post-operative tissue function and lung modeling.

INTRODUCTION

Advances in medical imaging have enabled clinicians to more accurately depict the anatomy of a patient, and therefore, more accurately identify diseases and the location of any diseased tissue. For example, medical imaging such as CT (including X-ray CT, computerized axial tomography (CAT) scan, positron emission tomography (PET), and single-photon emission CT (SPECT)) enable the development of three-dimensional reconstructions of anatomical structures. These three-dimensional models enable a clinician to identify and assess features of the modeled anatomical structure, thus facilitating the preoperative planning process.

Using medical imaging, such as CT, a clinician is able to accurately identify lesions or other medical conditions without the need for invasive surgeries (such as an open approach or thoracotomy). Three-dimensional reconstructions or models of organs, anatomical structures, or the like are developed using the images obtained using one of the above noted imaging modalities. Using the three-dimensional model, a clinician is able to segment various tissues from one another and assess an accurate location of the lesion within the thoracic cavity, or in one particular example, within the lungs. This segmentation further enables a clinician to determine the precise tissue segment with its affiliated vessel and bronchial branches and determine the ideal incision level for Video-Assisted Thoracoscopic Surgery (VATS) procedures (such as a segmentectomy, loboctomy, pneumonectomy, or the like).

The three-dimensional model and precise identification of the lesion within the lung and its associated vessel and bronchial branches enables clinicians to identify an ideal location for port placement and develop a pathway through which surgical instruments may be guided during the thoracoscopic procedure. Typically, a fiducial or other marker (e.g., a coil or wire) is implanted within the affected tissue with the aid of fluoroscopy or other imaging modalities. Thereafter, the location of the fiducial relative to the lesion is checked using imaging and the VATS procedure is performed.

SUMMARY

Aspects of the disclosure relate to systems and methods that facilitate the pre-operative prediction of post-operative tissue function, e.g., post-resection lung tissue function, thus assisting a clinician in planning for and carrying out a surgical procedure, e.g., determining the location(s) and volume(s) of lung tissue to be resected.

As used herein, the term "clinician" refers to a doctor, a nurse, or any other care provider and may include support personnel. The term "proximal" refers to the portion of the device or component that is closer to the clinician and the term "distal" refers to the portion of the device or component that is farther from the clinician. Additionally, terms such as front, rear, upper, lower, top, bottom, and similar directional terms are used as relative terms simply for convenience of description and are not limiting in nature. Further, to the extent consistent, any of the aspects and features detailed herein may be utilized in conjunction with any of the other aspects and features detailed herein.

Provided in accordance with aspects of the disclosure is a method of pre-operative surgical planning and a non-transitory computer-readable storage medium storing a program that, when executed by a processor, performs the method of pre-operative surgical planning. The method includes generating a pre-resection 3D model of a tissue structure, determining tissue function information for the pre-resection 3D model of the tissue structure, simulating, on the pre-resection 3D model, removal of a selected portion of tissue to produce a post-resection 3D model, and determining tissue function information for the post-resection 3D model of the tissue structure.

In accordance with the disclosure, a method includes determining the selected portion of tissue to be removed prior to the simulation. Determining the selected portion of tissue to be removed is based upon at least one of: an automatically-generated tissue resection line provided on the pre-resection 3D model or an input tissue resection line provided on pre-resection 3D model.

The method may further include displaying the pre-resection 3D model of the tissue structure on a user interface. The method may also include representing at least a portion of the determined tissue function information for the pre-resection 3D model of the tissue structure on the user interface with the pre-resection 3D model.

The method may further includes displaying the post-resection 3D model of the tissue structure on a user interface. The method may also include representing at least a portion of the determined tissue function information for the post-resection 3D model of the tissue structure on the user interface with the post-resection 3D model.

The tissue function information for the pre-resection 3D model or the post-resection 3D model may include at least one of: a level of tissue function; a metric indicative of tissue function; an abnormality affecting tissue function; or an indication of a disease affecting tissue function.

Additionally or alternatively, the tissue function information for the pre-resection 3D model or the post-resection 3D model may include at least one of: tissue density data; metabolic activity data; or pulmonary function test information.

Another method and/or non-transitory computer-readable storage medium for pre-operative surgical planning provided in accordance with aspects of the disclosure includes displaying a pre-resection 3D model of a tissue structure on a user interface and displaying one or more resection lines on the pre-resection 3D model. The method/storage medium further includes modifying and/or confirming the resection line(s), simulating, on the pre-resection 3D model, removal of a selected portion of tissue based upon the resection line(s) to produce a post-resection 3D model, and displaying the post-resection 3D model on the user interface. The post-resection 3D model represents remaining tissue differently from the selected portion of tissue removed.

The method may further include determining tissue function information for the pre-resection 3D model of the tissue structure, and representing at least a portion of the determined tissue function information on the pre-resection 3D model.

Additionally, the method may further include determining tissue function information for the post-resection 3D model of the tissue structure, and representing at least a portion of the determined tissue function information on the post-resection 3D model.

In aspects of the present disclosure, the method may further include displaying, on the user interface, the post-resection 3D model and another post-resection 3D model. The another post-resection 3D model is the result of a simulation of removal of a different selected portion of tissue based upon at least one different resection line.

According to another aspect of the disclosure, a system for modeling a lung is provided and includes a display and a computer. The computer has a processor and a memory coupled to the processor. The memory has instructions stored thereon which, when executed by the processor, cause the computer to generate a 3-D model of a lung based on imaging data of the lung, display on the display the 3-D model of the lung in a collapsed state, remove a section of the lung selected for excision, and display the 3-D model of the lung without the section of the lung selected for excision.

The displayed 3-D model of the lung without the section of the lung selected for excision may be displayed in an inflated state. Additionally or alternatively, the computer may be configured to determine an effect that the removal of the section of the lung has on the lung, modify the displayed 3-D model of the lung in the inflated state based on the determined effect, and display the modified 3-D model of the lung. The displayed 3-D model of the lung without the section of the lung selected for excision may be displayed in the collapsed state.

The computer may be configured to display a real-time image of a surface of a patient's lung, and display over the displayed surface of the patient's lung a 3-D model of the section of the lung selected for excision. The section of the lung selected for excision may be highlighted to differentiate the section of the lung selected for excision from the displayed surface of the patient's lung. Removing the section of the lung may include modifying the 3-D model of the lung in the collapsed state by removing the section of the lung from the 3-D model of the lung. The computer may be configured to highlight on the display the section of the lung selected for excision prior to removing the section of the lung from the displayed 3-D model.

In accordance with another aspect of the disclosure, a method of modeling a lung is provided and includes generating a 3-D model of a lung based on imaging data of the lung, displaying on the display the 3-D model of the lung in a collapsed state, and modifying the displayed 3-D model of the lung in response to a removal of a section of the lung selected for excision, such that the section of the lung selected for excision is not shown in the displayed 3-D model of the lung in the collapsed state.

The method may further include displaying the 3-D model of the lung in an inflated state. Additionally or alternatively, the 3-D model of the lung in the inflated state may be displayed without the section of the lung.

The method may further include determining an effect that the removal of the section of the lung has on the lung, and displaying the 3-D model of the lung in the inflated state based on the determined effect. Additionally he method may further include displaying a real-time image of a surface of the patient's lungs, and displaying over the displayed surface of the patient's lungs the section of the lung selected for excision. Further the method may include highlighting on the display the section of the lung selected for excision, thereby differentiating the section of the lung from the displayed surface of the lung. The imaging data may be computerized tomography (CT) scan data of the patient's lungs.

In accordance with yet another aspect of the disclosure, a system for modeling a lung is provided and includes a display and a computer. The computer has a processor and a memory coupled to the processor. The memory has instructions stored thereon which, when executed by the processor, cause the computer to display a 3-D model of a lung in a collapsed state, highlight a section of the 3-D model of the lung selected for excision, and display the 3-D model of the lung without the section of the lung selected for excision.

In aspects, the computer may be configured to display the 3-D model of the lung in an inflated state. The 3-D model of the lung in the inflated state may be displayed without the section of the lung selected for excision. Further, the computer may be configured to determine an effect that a removal of the section of the lung has on the remaining portion of the lung, and modify the displayed 3-D model of the remaining portion of the lung in the inflated state based on the determined effect. Additionally or alternatively, the computer may be configured to display a real-time image of a surface of a patient's lung, and display over the displayed surface of the patient's lung only the selected section of the 3-D model of the lung.

BRIEF DESCRIPTION OF THE DRAWINGS

Various aspects and features of the disclosure are described hereinbelow with reference to the accompanying drawings wherein like reference numerals identify similar or identical elements.

FIG. 5 is a flow diagram illustrating a method in accordance with aspects of the disclosure.

DETAILED DESCRIPTION

There is a continuing need for systems and methods that facilitate the pre-operative planning process. In particular, there is a need for systems and methods that facilitate the pre-operative prediction of post-operative tissue function to assist the clinician in planning for and carrying out a surgical procedure.

As such, the systems and methods discussed herein facilitate the pre-operative prediction of post-resection lung tissue function, thus assisting a clinician in determining the location(s) and volume(s) of lung tissue to be resected. However, although detailed herein with respect to pre-operative prediction of lung function after a lung resection procedure, the aspects and features of the disclosure may similarly be utilized with respect to pre-operative prediction of post-operative function of other tissue structures and/or after other surgical procedures.

Figure 1:
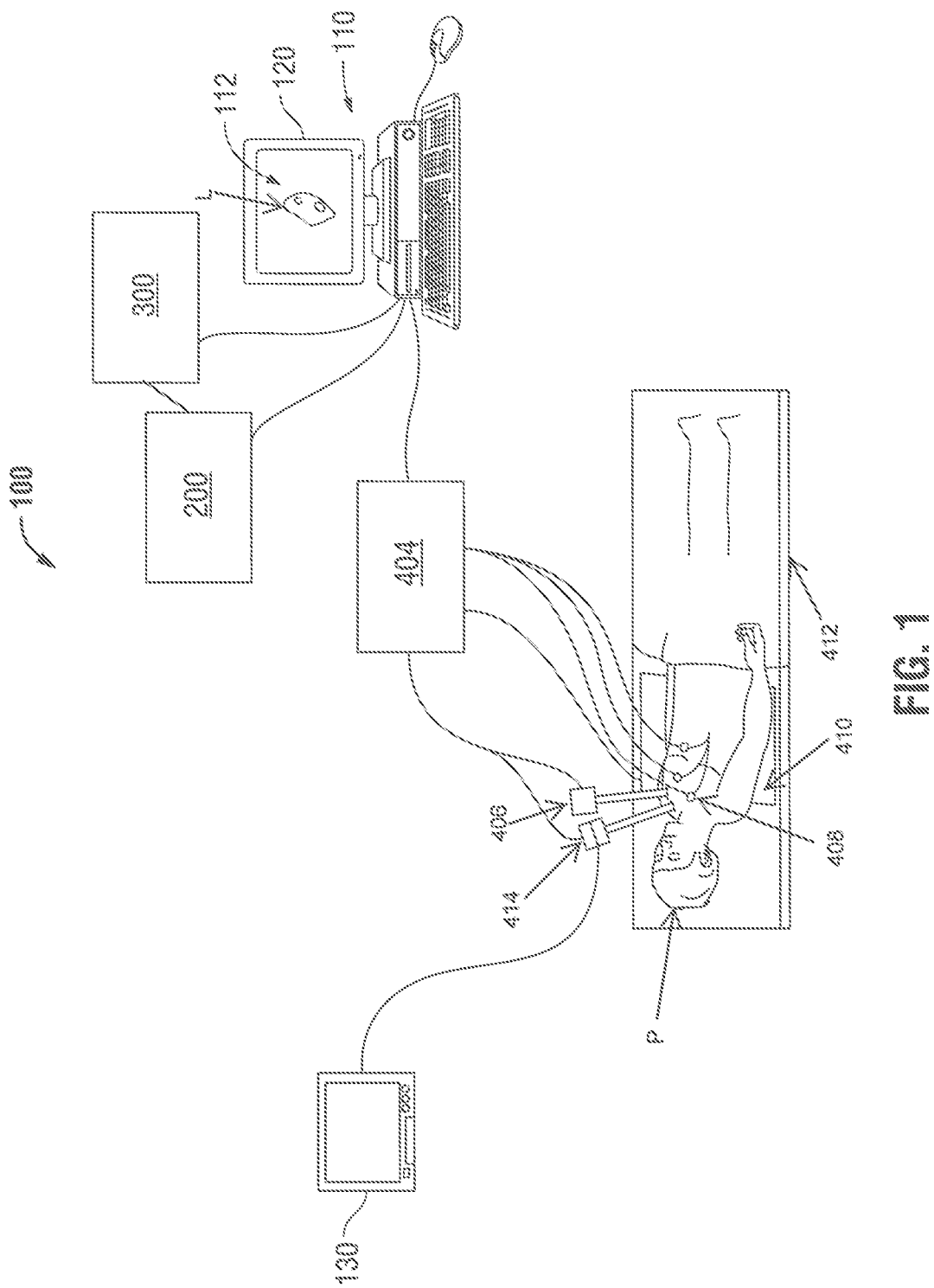
FIG. 1 is a perspective view of a surgical system provided in accordance with aspects of the disclosure.

FIG. 1 illustrates a system 100 that includes a computer 110 and a user interface 112 displayed on a suitable display 120 associated with computer 110 or any suitable monitoring equipment, e.g., an operating room monitor 130. In embodiments, user interface 112 may be remote from computer 110 and/or wirelessly connected to computer 110 or other component(s) of system 100. Although illustrated as a desktop computer in FIG. 1, computer 110 may be any suitable computing device, such as a desktop computer, laptop computer, tablet, smartphone, etc. System 100 further includes a Hospital Information System (HIS) 200, a synthesizer 300, and an operative surgical system 404. HIS 200 and synthesizer 300 are detailed below. The operative surgical system 404 is utilized during a surgical operation and may include, for example, a monitoring system, a visualization system, a tracking system, one or more surgical tools, etc.

Figure 2:
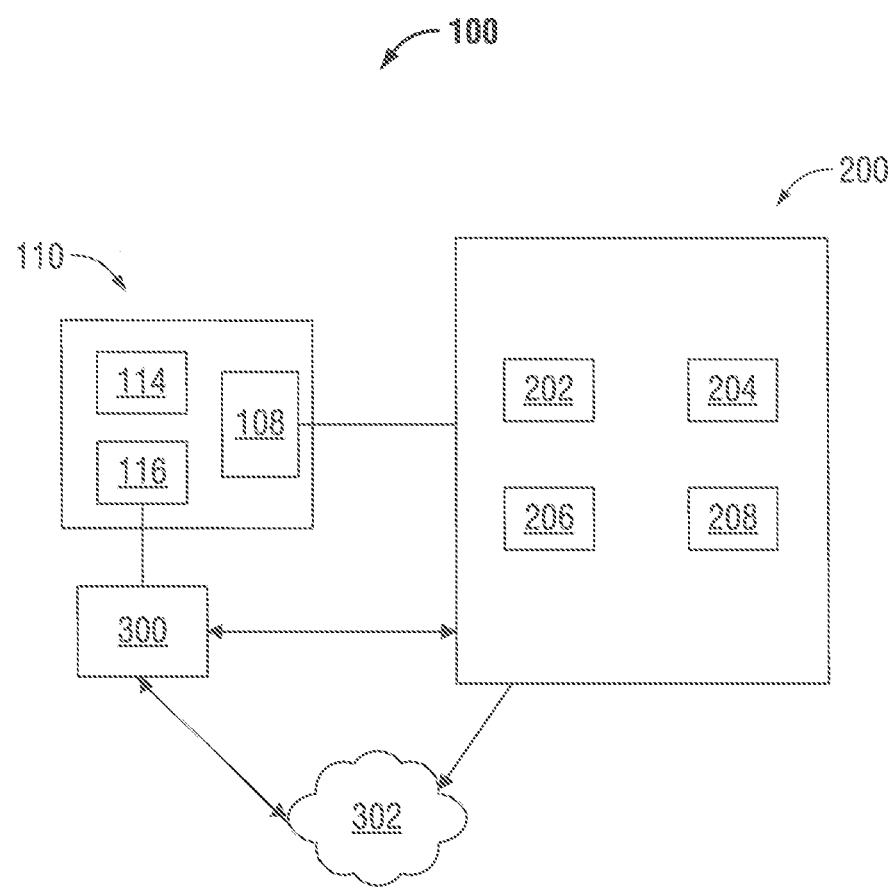
FIG. 2 is a block diagram illustrating a portion of the surgical system of FIG. 1.

Referring also to FIG. 2, computer 110 includes one or more processors 114 associated with one or more memories 116. Memory 116 may include any non-transitory computer-readable storage media for storing one or more software applications that are executable by processor 114. A network module 108 of computer 110 enables communication between computer 110 and a network to which HIS 200 and synthesizer 300 are also connected.

HIS 200 interfaces with a Picture Archiving and Communication System (PACS) 202, a Radiology Information System (RIS) 204, an Electronic Medical Records System (EMR) 206, and a Laboratory Information System (LIS) 208. PACS 202 stores and/or archives images of patients obtained from imaging systems such as, for example, X-ray CT, computerized axial tomography (CAT) scan, positron emission tomography (PET), single-photon emission CT (SPECT), Magnetic Resonant Imaging (MRI), Ultrasound (US), etc. MS 204 complements HIS 200 and PACS 202 and serves as an electronic management system for an imaging department of a hospital, e.g., allowing a clinician to access digital images of a patient and to associate patient information from EMR 206 with the digital images stored in PACS 202. LIS 208 supports data exchange between a hospital laboratory and HIS 200 and, in particular, EMR 206.

Synthesizer 300 includes a software application stored in a memory, e.g., memory 116, a memory of synthesizer 300, or another suitable memory, that is executable by a processor, e.g., processor 114, a processor of synthesizer 300, or another suitable processor. The software application of synthesizer 300 enables a clinician to access HIS 200 through network module 108 of computer 110 or via any other suitable computing device. More specifically, synthesizer 300 communicates with HIS 200 and provides a medium by which the clinician is able to gather data and utilize such data to, for example, pre-operatively predict lung function following a lung resection procedure, as detailed below. Synthesizer 300 may interface with a synthesizer cloud 302, e.g., using a hardwired connection or wirelessly, such that the synthesizer 300 may access HIS 200 remotely, e.g., via a device not connected to the intranet, or may interface directly with HIS 200 to provide local access, e.g., within the intranet.

Referring still to FIGS. 1 and 2, using information gathered from HIS 200 and/or other sources, synthesizer 300 produces a model of the lung(s), e.g., displayed on a user interface, e.g., user interface 112, to enable the clinician to visualize lung features and structures. More specifically, pre-operative image data gathered from HIS 200 is processed by the software application of synthesizer 300 to generate a three-dimensional (3D) model of the patient's lung(s) that is displayed to the clinician, e.g., on user interface 112. Additional medical information such as, for example, prior surgical procedure data, the location of common structures within the patient's body cavity, etc., may also be utilized in the generation of the 3D model. The pre-operative image data and/or additional medical information may be obtained from PACS 202, MS 204, EMR 206, LIS 208, and/or any other suitable source(s) of information.

Synthesizer 300 is further configured to gather information indicative of lung function and determine an estimated lung function of one or more portions of the lung based upon the indicative information. The indicative information and/or estimated lung function information may be integrated into the 3D model to enable the clinician to visualize, on the 3D model, the lung function (or information indicative thereof) of a particular volume or volumes of the lung, as detailed below. As such, the clinician is provided with information in a readily digestible manner, e.g., integrated into a 3D model, to facilitate pre-operative planning and, more specifically, the determination of the location and extent to which the lung is to be resected during a lung resection procedure. The estimated lung function information may further be integrated into the 3D model, to enable prediction of the estimated lung function of the portion of the lung remaining after resection of a selected volume of lung, as also detailed below. As such, the clinician can confirm whether the selected volume of lung to be resected is appropriate or whether modification is necessary.

The information indicative of lung function may be obtained from HIS 200, e.g., from PACS 202, MS 204, EMR 206, LIS 208, and/or any other suitable source(s) of information. The information indicative of lung function may include lung density information, which may be extracted from CT scan data or otherwise obtained. Lung density information can indicate volumes of hypodensity, where the density of the tissue is less than the surrounding tissue. Hypodense volumes of tissue may indicate that these portions are largely air with little to no tissue and, thus, provide poor to no lung function. Densities may be measured in Hounsfield units of HU, and may be represented directly on the 3D model either continuously, e.g., in a manner similar to a topographic map; utilizing one or more thresholds, e.g., indicating areas where the density is below a certain threshold (for example, 950 HU); or in incremental levels, e.g., identifying each volume of the lung as having low density, average density, or high density. Alternatively, the density information of a volume may be factored into the determination of estimated lung function of that volume.

The information indicative of lung function may additionally or alternatively include, for example, the presence, size, and location of an abnormality, e.g., adhesions, lesions, and/or the like, on the lung. Such information may be represented directly on the 3D model in corresponding size, shape, and location, and/or may be factored into the determination of estimated lung function of the volume where the abnormality is located.

The information indicative of lung function may additionally or alternatively include metabolic activity information. More specifically, PET imaging data may be utilized to identify volumes of low metabolic activity, indicating such volumes are mostly comprised of air with little to no tissue and, thus, provide poor to no lung function. Metabolic activity data may be represented directly on the 3D model either continuously, e.g., in a manner similar to a topographic map; utilizing one or more thresholds, e.g., indicating areas where the metabolic activity is below a certain threshold; or in incremental levels, e.g., identifying each volume of the lung as having low metabolic activity, average metabolic activity, or high metabolic activity. Alternatively, the metabolic activity data for a volume may be factored into the determination of estimated lung function of that volume.

Additional or alternative information indicative of lung function may include information regarding diseased areas of the lung, e.g., from conditions such as COPD, emphysema, COPD, ILD, fibrosis, asthma, cancer, etc. Such information may be recognized from CT image data obtained from PACS 202 of HIS 200, or may be obtained from another source such as, for example, previous determinations of lung disease indicated in EMR 206 of HIS 200.

Information indicative of lung function may also include Pulmonary Function Test (PFT) information such as, for example, Forced Expiratory Volume in the first one second of expiration ($FEV_1$), Forced Vital Capacity (FEC), Total Lung Capacity (TLC), Functional Residual Capacity (FRC), etc.).

Lung function information may be provided on the 3D model in one or more clinician-selectable layers such as for example, a layer incorporating the tissue density data, a layer incorporating the abnormality data, a layer incorporating the metabolic activity data, a layer incorporating the diseased areas information, etc. As such, in embodiments, the clinician may select the information to be provided (and also that to be excluded). Alternatively or additionally, levels of lung function determined using the above-noted lung function information may be represented on the 3D model using, for example, indicia, color coding, etc. Further, lung function levels may be provided continuously, e.g., using a progressive shading scheme, or may be provided discretely, e.g., using discrete lung function "ratings" each having a color or pattern associated therewith. Likewise, lung function may be indicated continuously across the lung, or the lung may be sectioned into volume segments or regions with a lung function level assigned to each segment or region.

The software application of synthesizer 300 may automatically select, utilizing the above-noted lung function information and/or other information gathered from EMR 204 of HIS 200, and display, e.g., on user interface 112, suggested resection lines on the 3D model. The clinician may move or otherwise modify the suggested resection lines, e.g., utilizing the above-noted lung function information and/or other information as a guide. Alternatively or additionally, the clinician may "draw" resection lines on the 3D model using any suitable input device, e.g., a mouse, joy-stick, touch-screen display, etc. The software application of synthesizer 300 may further analyze the placement of the resection lines on the 3D model to identify potential placement issues based upon information gathered from EMR 204 or based upon medical information regarding sensitive formations and/or vasculature within the lung. The resection lines may then be further modified and, finally, set for simulation and the simulation run.

Figure 4:
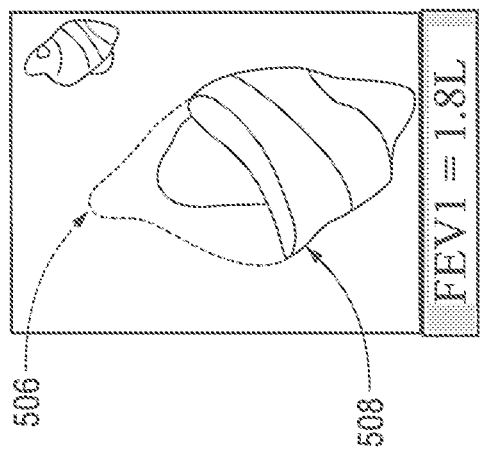
FIG. 4 is another illustration of the user interface of the system of FIG. 1, displaying a 3D model of a patient's lung including lung function information and indicating portions of the patient's lung selected for removal.
Figure 3:
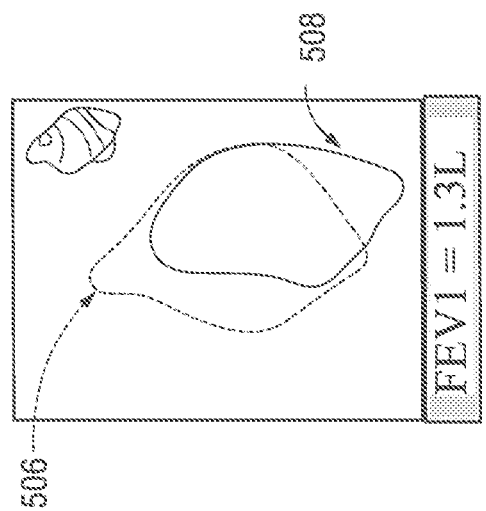
FIG. 3 is one illustration of the user interface of the system of FIG. 1, displaying a 3D model of a patient's lung indicating portions of the patient's lung selected for removal.

FIGS. 3 and 4 illustrate displays of the 3D model on a user interface, e.g., user interface 112, including a representation of the lung after the resection simulation has been run, based upon the selected resected lines. The lung volume removed may be illustrated in a first manner while the lung volume that remains is illustrated in a different manner, e.g., using different coloring, indicia, shading, line styles, etc. In this manner, each lung volume can be readily identified by the clinician. In embodiments, a rendering of the 3D model from the resultant simulation, as detailed above, is provided at one portion of the user interface (e.g., at a center portion), with the remaining lung volume 508 illustrated solidly and/or in color and the removed lung volume 506 illustrated in phantom and/or grayscale. In addition, a depiction of the full 3D model (before the simulated resection) including the lung function information, as detailed above, may be provided at another portion of the user interface (e.g., at a corner or the like). The lung function information may likewise be represented in the simulation resultant 3D model such as, for example, as illustrated in FIG. 4.

In addition to the simulations and representations of the 3D model, predicted post-operative lung function details may likewise be displayed (or otherwise output). For example, as also illustrated in FIGS. 3 and 4, based upon the volume to be resected and the estimated lung function and other information relating to the removed and/or remaining volume, the software application of synthesizer 300 may predict and display one or more estimated post-operative metrics, e.g., $FEV_1$, FEC, TLC, FRC, the level of lung deflation during single lung ventilation surgery, etc. The metric is updated as the resection lines and, thus, the volume to be resected, is altered. Thus, for example, the predicted $FEV_1$ based upon the volume removed as indicated in FIG. 3 is different from the predicted $FEV_1$ based upon the volume removed as indicated in FIG. 4.

The estimated post-operative metric(s) may be provided in absolute terms, e.g., in their respective units, and/or may be provide relatively, e.g., as a percentage of the pre-operative values. A comparison mode is also contemplated, enabling the clinician to compare the predicted post-operative lung function after resection of a first volume of lung versus that after a resection of a second, different volume of lung. This may be provided, for example, by providing a split-screen display on user interface 112, whereby both the first simulated resection and the second simulated resection are provided, e.g., displaying both the illustrations of FIGS. 3 and 4 side-by-side, top-and-bottom, etc., on user interface 112.

Once the clinician is satisfied with the predicted post-operative lung function, the resection lines corresponding thereto may be utilized in preparation for and/or during the lung resection procedure to achieve the desired result. If not satisfied, the clinician may modify one or more of the resection lines and re-run the simulation as many times as necessary until the clinician is satisfied with the predicted post-operative lung function.

Turning to FIG. 5, in use, a pre-resection 3D model of a tissue structure, e.g., a patient's lung, is initially generated (S510) and, in embodiments, is provided, e.g., displayed, to a clinician (S520). Tissue function information for the tissue structure is determined from the pre-resection 3D model (S530) and provided (S540), e.g., displayed.

A portion of tissue on the pre-resection 3D model is selected for removal (S550), automatically or manually, based upon, for example, the pre-resection tissue function information. This may be accomplished via one or more resection lines, as detailed above. Once the portion of tissue to be removed is selected (and confirmed), removal of that portion of tissue is simulated on the pre-resection 3D model to produce a post-resection 3D model (S560) that, in embodiments, is provided, e.g., displayed, to the clinician (S570).

Tissue function information for the post-resection 3D model, e.g., for the remaining tissue, is then determined (S580) and provided, e.g., displayed, to the clinician (S590) such that, for example, the clinician may determine whether or not the predicted post-operative lung function is satisfactory (S600). If the clinician is satisfied ("YES" at S600), the pre-operative surgical planning method ends ("END"). If the clinician is not satisfied ("NO" at S600), the method returns to S550, allowing a different portion of tissue on the pre-resection 3D model to be selected for removal, based upon which a post-resection 3D model may be generated, a simulation may be run, and tissue function information determined and provided (see S560-S590). Where multiple simulations and post-resection 3D models are run, the clinician may compare results from each, as noted above, to facilitate determining the appropriate portion of tissue to be resected.

A further aspect of the disclosure is directed to improving the outcomes of the lung surgeries modeled above. Typically, the lung surgeries seek to limit the excised material of the lung through removal of only selected anatomical sub-lobar segments (in multiple or single configuration) or a non-anatomical sub-lobar wedge. Lung surgeries are generally performed when the lung is in a collapsed state. However, in its collapsed state the lung does not appear to the surgeon in the same state as in preoperative CT scans, described above. Small landmarks such as fissures on a deflated lung may be difficult for the surgeon to find when the lung is in the deflated state. The surgeon's success rate can be increased through better situational awareness by providing new landmarks to replace or augment the natural landmarks to which the surgeon may be accustomed. The disclosure provides systems and methods for modeling an excision of lung tissue before the lung is re-inflated.

To improve success rates, during preoperative planning the 3-D model of the lung is displayed in a collapsed state. Once collapsed, the surgeon can cycle through all lobes, segments, and wedges, with each independently displayed in the 3-D model through a color change or any other suitable method. The surgeon can use the 3-D model of the collapsed lung to identify the minimal amount of lung to excise that will still remove the lesion within the required margin. The surgeon may toggle on and off various segments and wedges of the lung to identify those that will meet the surgical criteria. The display system may recommend appropriate dissection points and give the surgeon feedback on the current selection's margin. The system may also calculate the size of the excised material and provide information on the size of the port or incision, specimen bag, nearest extraction location/incision required for removal from the body. Once a decision on what to excise has been made, the excised material is removed from the model and the lung is re-inflated to show how the removed material will affect the patient's overall physiology, including the remaining lung tissue and adjacent structures, similar to the methods described above. The system may interface with a database that stores data of prior procedures involving removal of a lung section and how the remaining lung responded to the removal. During surgery, the surgical plan is projected into the surgeon's view highlighting the lobe, segments, and wedges that were selected for excision. The highlighted lung tissue would overlay the now-inflated lung.

As illustrated in FIG. 1, the methods described below utilize the surgical system 100 including a navigation system capable of guiding a surgical tool 406 within the thoracic cavity and the patient's "P" lungs "L" to an area of interest, such as, for example, a section "S" of lung tissue selected for excision. The operative surgical system 404 includes a tracking application that is configured for use with the surgical tool 406 and enables monitoring of the position and orientation of a distal portion of the surgical tool 406. operative surgical system 404 may be an electromagnetic navigation system utilized to guide the surgical tool 406 through the thoracic cavity and/or lungs "L" of the patient "P." The operative surgical system 404 includes a plurality of reference sensors 408, and a transmitter mat 410. The surgical tool 406 has a sensor (not shown) disposed at a distal portion thereof that enables monitoring of the position and orientation of the distal portion of the surgical tool 406, in six degrees of freedom, relative to a reference coordinate system. Patient "P" is shown lying on an operating table 412 with the surgical tool 406 advanced within the thoracic cavity using any suitable surgical device capable of permitting a surgical instrument to pass through a patient's "P" chest, such as an access port, trocar, or the like (not shown).

The preoperative portion of a method for modeling the lungs of a patient "P" using CT imaging data will now be described. Initially, the lungs (while in an inflated state) of a patient "P" are imaged using any suitable imaging device, such as, for example, a CT device (not shown). The CT device may include X-ray CT, computerized axial tomography (CAT) scan, positron emission tomography (PET), or single-photon emission CT (SPECT). The imaging data is stored within the memory 116 (FIG. 1) of the computer 110. In some embodiments, the image data may be stored within a memory associated with a remote computer or network (not shown) such as a distributed network or the internet via a wired or wireless connection for the transmission and reception of data to and from other sources.

Following imaging of the patient, a software application stored within the memory 116 is executed by the processor 114 to enable review of the image data. An area of interest illustrating the effects of lung disease (e.g., emphysema, COPD, asthma, cancer, or the like) is identified in the images and its location determined within the lungs "L" of the patient "P." Several imaging methods used for identifying an area of interest are contemplated such as ultrasound, CT scan, metabolic scanning, or the like. In one embodiment, where the patient "P" is not suffering from easily identified lesions or cancers of the lungs, the results of images generated from a previously acquired CT scan can be analyzed to identify areas of hypodensity. In an alternative embodiment, PET imaging may be utilized to identify areas of low metabolic activity within the lungs "L". After analysis of the image data, using one of the above described techniques, the location of the area of interest within the lungs may be identified and its location stored within the memory 116 (FIG. 1) of the computer 110.

Figure 6A:
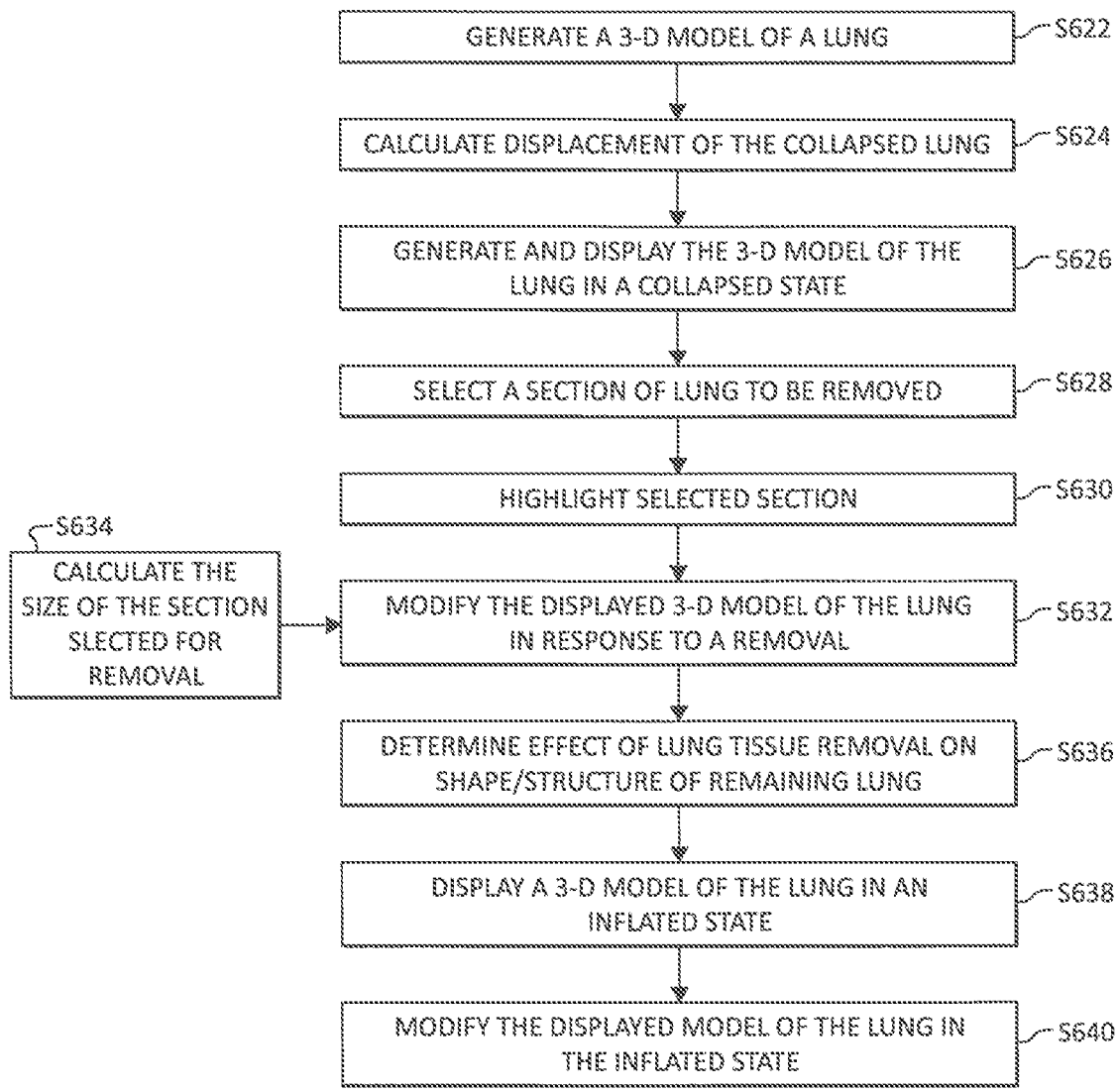
FIG. 6A is a flow chart showing a pre-operative portion of a method of modeling a lung.

FIG. 6A shows a flow chart illustrating a pre-operative portion of a method of modeling a lung in accordance with the disclosure. In step S622, the image data is processed by the software application stored within the memory 116 to generate a 3-D model reconstruction of the CT images of the patient's lung using any suitable method. The software application employs one of a variety of rendering techniques and processing algorithms to isolate, identify, and/or generate a 3-D volumetric rendering of the lungs (in an inflated state) for presentation to the clinician on the display 120. A segmentation algorithm is applied to the 3-D model reconstruction to define the boundaries of various types of tissue by comparing the values of each data element of the 3-D reconstruction to a series of thresholds of other similar criteria, such as using density and continuity. The segmentation algorithm groups together similar types of tissue based upon the outcome of the comparison, and in one embodiment, may differentiate low contrast density details of the lung (e.g., lung parenchyma, pleura fissure lines, bronchi, and the like) from high contrast density details of the lung (e.g., luminal structures, hilar structures, bronchopulmonary lymph nodes, and the like). It is envisioned that the software application may utilize any suitable segmentation algorithm known in the art. The software application may present each segmented group as a different color or different transparency level that may be selectively adjusted by the clinician in order to enable the clinician to better identify each segmented or differentiated group. It is further contemplated that the software application may illustrate identified structures as opaque and unidentified structures as translucent, or vice versa.

In step S624, the displacement of the collapsed lung is calculated in preparation for transforming the 3-D construction of the inflated lungs into a 3-D construction of the lungs in a collapsed state, as the lungs would typically appear during a surgical procedure. When subjected to compression, the various structures of the lungs deform or compress at differing rates and by differing volumes. To account for differences in elasticity, the clinician assigns each identified volume an elastic modulus, which is utilized by the software application when calculating the deformed (e.g., compressed) model of the lung. Additional properties, such as Poisson's ratio or the like, may be assigned to the differentiated structures, and in particular, to the lung parenchyma, which has a variable compressibility stemming from removal of air during the deflation of the lung. The software application may assign higher or lower elastic properties to non-structural portions of the pre-deflation lung volume based on the CT data or by manual input by the clinician. In this manner, tumor (or other lesion) volumes can be assigned a more rigid behavior (e.g., less prone to being compressed) and the displacement of the model will be recalculated accordingly. Additionally, it is contemplated that the software application may use information from patient electronic medical records (EMR) to estimate a more likely level of lung deflation as the elastic properties of the lung tissues will be affected by common lung conditions such as chronic obstruction pulmonary disorder (COPD).

The computer 110 (FIG. 1) may be configured to apply the directional effect of gravity on the 3-D model to more accurately calculate the displacement of the collapsed lung (e.g., determine the overall shape and structure of the lungs in a collapsed state). It is envisioned that any suitable algorithm for applying the directional effect of gravity may be utilized. The orientation of the 3-D model shown on the display 120 (FIG. 1) should be known in order to accurately apply the directional effect of gravity. Accordingly, if the clinician has already rotated the 3-D model to appear in the lateral decubitus position, the directional effect of gravity will be applied to the 3-D model such that the gravitational force acts in a lateral direction with respect to the 3-D model. Once the directional effect of gravity has been applied to the 3-D model, as the clinician rotates the 3-D model within the display 120, the direction of the gravitational force will readjust with respect to the 3-D model to ensure that the gravitational force is acting upon the 3-D model in the correct direction.

Figure 7A:
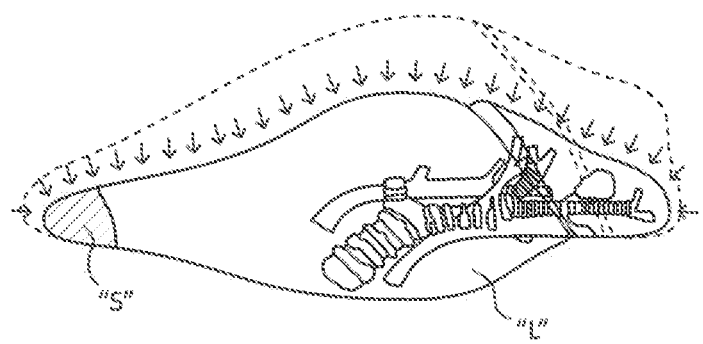
FIG. 7A is a side, cross-sectional view of a 3-D model of the patient's lungs showing the lungs in a collapsed state.

Following calculation of the displacement of the collapsed lungs, the 3-D model of the lung in the collapsed state is generated and displayed on the display 20 in step S626, as illustrated by way of example in FIG. 7A. It is contemplated that any suitable model may be employed to calculate the displacement of the collapsed lung, such as a linear elastic model or a hyperelastic model (e.g., the Saint Venant-Kirchhoff model, the Fung model, or the Mooney-Rivlin model), although other suitable hyperelastic models may also be employed. The type of displacement model employed may be selected depending upon the type of tissue being analyzed.

Once the 3-D reconstruction is generated and segmentation has been completed, the software application may apply a secondary smoothing algorithm to prepare the 3-D reconstruction for meshing. In embodiments, segmentation and meshing may be completed using the Emprint® ablation system or superDimension® navigation system marketed and sold by Medtronic PLC. The resulting meshed 3-D model forms a Computational Lung Model (CLM), which is the 3-D model of the collapsed lung that is displayed to the clinician on the display 120 or the monitoring equipment 130 during the surgical procedure.

In step S628, the surgeon selects a section "S" (FIG. 7A) of the lung (e.g., diseased tissue) for excision or removal. Upon selecting the section "S" of lung for excision, in step S630, the section of the lung selected for excision is shown highlighted on the display 120 in a manner to differentiate the selected section "S" from the remainder of the displayed lung "L". For example, the selected section "S" may be shown in a different color from the remainder of the lung "L" or be shown darker or lighter than the remainder of the lung "L".

Figure 7B:
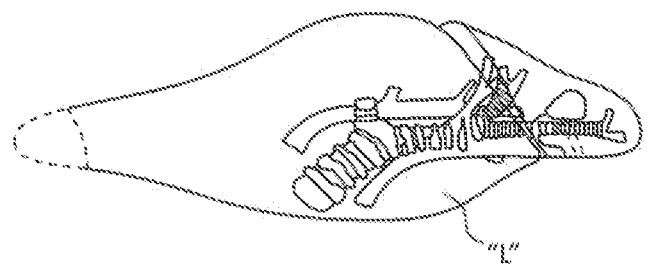
FIG. 7B is a side, cross-sectional view of the 3-D model shown in FIG. 3A with a section of lung tissue removed.

The surgeon may indicate that the selected section is to be removed, whereby in step S632, the displayed 3-D model of the collapsed lung "L" is modified. In particular, in response to a decision to remove the section of the lung "L" selected for excision, the highlighted section of the lung "L" disappears from the displayed 3-D model of the lung, as illustrated by way of example in FIG. 7B. In one aspect, modifying the displayed 3-D model of the collapsed lung "L" may include the system 100 generating and displaying an entirely new visual representation (e.g., a 3-D model) of the lung in a collapsed state without the section "S." In another aspect, modifying the displayed 3-D model of the collapsed lung "L" may include modifying the same visual representation (e.g., 3-D model) of the lung in the collapsed state by removing the section "S" from the displayed 3-D model of the lung. In either of these aspects, the displayed 3-D model may be modified by passing a slicing plane through the 3-D model, thereby separating the underlying mesh of the 3-D model into two parts. A hollow interior of the original mesh may be exposed where the two parts were originally connected so a new mesh for each part is used to place a solid surface where the segmenting plane passed through. The original 3-D model may be saved to allow toggling back and forth or deleted to save memory.

In some aspects of the disclosure, the computer 110 is configured to toggle on and off various segments and wedges of the lung "L" in response to a selection of the respective segments or wedges of the lung by the surgeon.

In step S634, the computer 10 may calculate a size of the section "S" of the lung "L" selected for excision, which may be used to determine the size of the port or incision through which the section "S" will be withdrawn from the surgical site. The calculation may be done by volumetric computation based on the shape of the removed section. For example, the calculation may include an approximation of the curved surfaces of the section "S" or integration over a surface equation that approximates the actual surface.

Upon processing the decision to remove the selected section "S" of the lung "L", the computer, in step S636, may determine an effect that the removal of the section of the lung "L" has on an overall shape or structure of the remaining lung "L". In step S638, the 3D-model of the lung "L" is shown in the inflated state without the section selected for removal. In step S640, the shape or structure of the displayed 3-D model of the lung "L" in the inflated state is modified based on the determination of the effect that the removal of the section of lung "L" would have on the remaining lung "L". In this way, the display 120 provides the clinician an estimation of how the overall physiology of the patient's lungs "L" will change after removing the selected section of the lung "L".

To assist in predicting the effect of the removal of the selected section of the lung "L", patient data may be input into the system 100 corresponding to the patient's vitals, such as pulmonary function (through a Pulmonary Function Test, blood gas analysis, or the like), cardiac function (i.e., heart rate or the like), respiration rate, oxygen saturation, and breathing effort. This information may also be input into a database (not shown) associated with the system 100. Additionally, identifying information such as age, sex, height, weight, race or national origin, and other information such as disease type, planned procedure, and patient's medical history may be input into the system 100. Over time, a database may be built using the data obtained during each procedure. This database may be indexed such that clinicians may review data obtained from similar patients to better predict the outcome of the procedure. Images of the patient obtained by a suitable imaging device may be correlated or indexed to the patient data to enable a clinician to look up similarly situated patients. In this manner, the system 100 of the disclosure may better predict the outcome of removing a selected section of the lung "L". The type of treatment being proposed, the volume of the treatment area including the amount of tissue being treated, the type of tissue being targeted, dynamic measures of integrated function (e.g., the six minute walk test), and qualitative metrics (e.g., St. Georges Respiratory Questionnaire) may be recorded and correlated to the patient data. The above described information gathered from other patients may be used to predict the effect of removal of the selected section of the lung "L". The software application compares the current patient's characteristics and the location of the selected section to the entries populating the database, and using a mathematical computation or other suitable algorithm, identifies a particular patient or set of patients to which the current patient substantially corresponds. Using this information, the computer determines the effect of removing that particular section of the lung "L" on the remaining lung "L" (e.g., which portions of the remaining lung "L" will expand or otherwise shift and to what extent).

At this point, the preoperative constructs of the CLM are complete, and the clinician may proceed to preoperative planning utilizing the CLM generated as a result of the procedure described hereinabove. After preoperative planning is complete, the procedure begins.

Figure 6B:
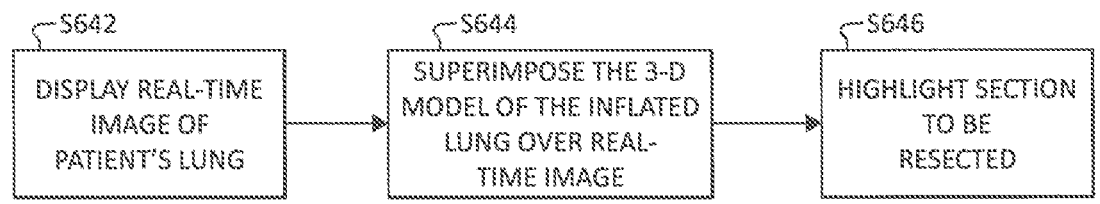
FIG. 6B is a flow chart showing an intra-operative portion of the method of modeling the lung.

With reference to the flow chart depicted in FIG. 6B, in step S642, a thoracoscope 414 (FIG. 1) is advanced within the thoracic cavity and video images are captured and transmitted to the display 120, providing a real time view of the patient's lung "L". In step S644, the 3-D model of the inflated lung "L" generated in step S618 is then superimposed over the real-time view of the lungs "L." In step S646, the section of the lung "L" selected for excision is highlighted on the display 20 or 30, thereby differentiating the section of the lung "L" from the displayed real-time view of the patient's lungs "L". VATS or iVATS may be utilized to navigate the surgical tool 406 to the selected section "S" of the lung "L". Once the surgical tool 406 has been successfully navigated to the selected section "S" of the lung "L", the clinician may remove or otherwise treat the selected section "S" of the lung "L" using the surgical tool 406.

As used herein, the term "clinician" refers to a doctor, a nurse, or any other care provider and may include support personnel. Although generally described herein as the various determination and/or selection steps being performed by a clinician, it is contemplated that the determination and/or selection steps described herein may be performed by the software application, or a combination of clinician and software application input. As can be appreciated, in certain instances, it may be necessary for the software application to make certain determinations, whereas in other instances it may be necessary for the clinician to make certain determinations. In embodiments, the software application may make a determination and present the determination to the clinician for selection and/or confirmation. In other embodiments, it may be necessary for the software application to provide a prompt or other warning to the clinician regarding the consequences of the clinician's decision, or to provide an alternative selection to the clinician, or combinations thereof. In the following description, well-known functions or constructions are not described in detail to avoid obscuring the disclosure in unnecessary detail.

Although the systems and methods detailed herein are generally described with respect to the lungs, it is contemplated that the following systems and methods may be applied to other organs such as, for example, the liver or the spleen. Further, while several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

What is claimed is:

1. A method of pre-operative surgical planning, comprising:
   generating a pre-resection 3D model of a tissue structure;
   displaying the pre-resection 3D model of the tissue structure on a user interface;
   simulating, on the pre-resection 3D model, collapsing the tissue structure to generate a collapsed pre-resection 3D;
   displaying the collapsed pre-resection 3D model;
   selecting a portion of tissue to remove from the collapsed pre-resection 3D model;
   simulating inflation of the tissue structure with the selected position of tissue removed to generate an inflated post-resection 3D model; and
   displaying the inflated post-resection 3D model.

2. The method according to claim 1, further comprising determining tissue function information for the pre-resection 3D model of the tissue structure.

3. The method according to claim 1, further comprising determining tissue function information for the inflated post-resection 3D model of the tissue structure.

4. The method according to claim 3, further comprising representing at least a portion of the determined tissue function information for the pre-resection 3D model of the tissue structure on the user interface with the pre-resection 3D model.

5. The method according to claim 3, further comprising representing at least a portion of the determined tissue function for the inflated post-resection 3D model of the tissue structure on the user interface with the inflated post-resection 3D model.

6. The method according to claim 1, further comprising determining the selected portion of the tissue to be removed, wherein determining the selected portion of tissue to be removed is based upon an automatically-generated tissue resection line provided on the collapsed pre-resection 3D model.

7. The method according to claim 6, further comprising modifying the automatically-generated tissue resection line, and wherein determining the selected portion of tissue to be removed is based upon the modified automatically-generated tissue resection line.

8. The method according to claim 1, further comprising determining the selected portion of tissue to be removed, wherein determining the selected portion of tissue to be removed is based upon a user input tissue resection line provided on the collapsed pre-resection 3D model.

9. A method of pre-operative surgical planning, comprising:
    simulating collapsing a tissue structure to generate a collapsed pre-resection 3D model;
    simulating, on the collapsed pre-resection 3D model, removal of a selected portion of tissue based upon at least one resection line provided on the collapsed pre-resection 3D model;
    simulating inflation of the tissue structure with the selected portion of tissue removed to generate an inflated post-resection 3D model; and
    displaying the inflated post-resection 3D model on a user interface.

10. The method according to claim 9, further comprising determining tissue function information for the inflated post-resection 3D model of the tissue structure.

11. The method according to claim 10, further comprising representing, on the user interface, at least a portion of the determined tissue function information on the inflated post-resection 3D model.

12. The method according to claim 9, wherein the at least one resection line provided on the collapsed pre-resection 3D model is automatically generated.

13. The method according to claim 12, further comprising modifying the automatically-generated tissue resection line.

14. The method according to claim 9, wherein the at least one resection line provided on the collapsed pre-resection 3D model is an input tissue resection line.

15. A non-transitory computer-readable storage medium storing a program that, when executed by a processor, performs the steps of:
    generating a pre-resection 3D model of a tissue structure;
    displaying the pre-resection 3D model of the tissue structure on a user interface;
    simulating, on the pre-resection 3D model, collapsing the tissue structure to generate a collapsed pre-resection 3D model;
    displaying the collapsed pre-resection 3D model;
    selecting a portion of tissue to remove from the collapsed pre-resection 3D model;
    simulating inflation of the tissue structure with the selected position of tissue removed to generate an inflated post-resection 3D model; and
    displaying the inflated post-resection 3D model.

16. The non-transitory computer-readable storage medium according to claim 15, further comprising determining tissue function information for the inflated post-resection 3D model of the tissue structure.

17. The non-transitory computer-readable storage medium according to claim 16, further comprising representing at least a portion of the determined tissue function information on the inflated post-resection 3D model.

18. The non-transitory computer-readable storage medium according to claim 16, further comprising determining the selected portion of the tissue to be removed, wherein determining the selected portion of tissue to be removed is based upon an automatically-generated tissue resection line provided on the collapsed pre-resection 3D model.

19. The non-transitory computer-readable storage medium according to claim 16, further comprising determining the selected portion of tissue to be removed, wherein determining the selected portion of tissue to be removed is based upon a user input tissue resection line provide on the collapsed pre-resection 3D model.

20. The non-transitory computer-readable storage medium according to claim 15, further comprising determining tissue function information for the pre-resection 3D model of the tissue structure.

* * * * *